United States Patent

Daines

Patent Number: 5,569,677
Date of Patent: Oct. 29, 1996

[54] DIPHENYL-2-PROPENOATES FOR TREATING DISEASES ASSOCIATED WITH LEUKOTRIENE B4

[75] Inventor: Robert A. Daines, Lansdale, Pa.

[73] Assignee: SmithKline Beecham Corporation, Philadelphia, Pa.

[21] Appl. No.: 464,174

[22] Filed: Jun. 5, 1995

Related U.S. Application Data

[63] Continuation of PCT/US94/13966, Dec. 5, 1994.

[51] Int. Cl.$^6$ .................................................. A61K 31/19
[52] U.S. Cl. ........................ 514/570; 514/563; 562/426; 562/429; 562/451
[58] Field of Search .................................... 562/462, 429, 562/431, 451; 514/563, 570

Primary Examiner—Samuel Barts
Attorney, Agent, or Firm—James M. Kanagy; Stephen Venetianer; Edward T. Lentz

[57] ABSTRACT

This invention relates to a compound of formula I

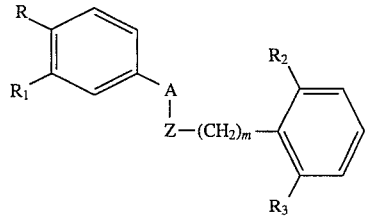

where the several groups are defined herein. These compounds are leukotriene antagonists and as such can be used in treating various diseases associated with leukotrienes.

8 Claims, No Drawings

DIPHENYL-2-PROPENOATES FOR TREATING DISEASES ASSOCIATED WITH LEUKOTRIENE B4

This is a continuation of PCT application Ser. No. PCT/US94/13966 filed 5 Dec. 1994 which claimed priority from U.S. Ser. No. 08/164,604, filed on Dec. 9, 1993.

SCOPE OF THE INVENTION

The field of this invention is that of certain substituted diphenyl-2-propenoates, and homologs thereof, which have been found to be useful for treating diseases arising from or related to leukotrienes, particularly leukotriene $B_4$. As such there utility lies in antagonizing the affects of leukotrienes.

BACKGROUND OF THE INVENTION

The family of bioactive lipids known as the leukotrienes exert pharmacological effects on respiratory, cardiovascular and gastrointestinal systems. The leukotrienes are generally divided into two sub-classes, the peptidoleukotrienes (leukotrienes $C_4$, $D_4$ and $E_4$) and the dihydroxyleukotrienes (leukotriene $B_4$). This invention is primarily concerned with the hydroxyleukotrienes (LTB) but is not limited to this specific group of leukotrienes.

The peptidoleukotrienes are implicated in the biological response associated with the "Slow Reacting Substance of Anaphylaxis" (SRS-A). This response is expressed in vivo as prolonged bronchoconstriction, in cardiovascular effects such as coronary artery vasoconstriction and numerous other biological responses. The pharmacology of the peptidoleukotrienes include smooth muscle contractions, myocardial depression, increased vascular permeability and increased mucous production.

By comparison, $LTB_4$ exerts its biological effects through stimulation of leukocyte and lymphocyte functions. It stimulates chemotaxis, chemokinesis and aggregation of polymorphonuclear leukocytes (PMNs).

Leukotrienes are critically involved in mediating many types of cardiovascular, pulmonary, dermatological, renal, allergic, and inflammatory diseases including asthma, adult respiratory distress syndrome, cystic fibrosis, psoriasis, and inflammatory bowel disease.

Leukotriene $B_4$ ($LTB_4$) was first described by Borgeat and Samuelsson in 1979, and later shown by Corey and co-workers to be 5(S),12(R)-dihydroxy-(Z,E,E,Z)- 6,8,10,14-eicosatetraenoic acid.

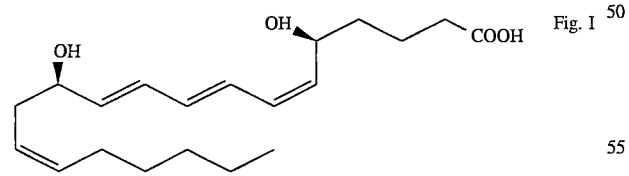

Fig. I

It is a product of the arachidonic acid cascade that results from the enzymatic hydrolysis of $LTA_4$. It has been found to be produced by mast cells, polymorphonuclear leukocytes, monocytes and macrophages. $LTB_4$ has been shown to be a potent stimulus in vivo for PMN leukocytes, causing increased chemotactic and chemokinetic migration, adherence, agggregaton, degranulation, superoxide production and cytotoxicity. The effects of $LTB_4$ are mediated through distinct receptor sites on the leukocyte cell surface that exhibit a high degree of stereospecificity. Pharmacological studies on human blood PMN leukocytes indicate the presence of two classes of $LTB_4$-specific receptors that are separate from receptors specific for the peptide chemotactic factors. Each of the sets of receptors appear to be coupled to a separate set of PMN leukocyte functions. Calcium mobilization is involved in both mechanisms.

$LTB_4$ has been established as an inflammatory mediator in vive. It has also been associated with airway hyper-responsiveness in the dog as well as being found in increased levels in lung lavages from humans with severe pulmonary dysfunction.

By antagonizing the effects of $LTB_4$, or other pharmacologically active mediators at the end organ, for example airway smooth muscle, the compounds and pharmaceutical compositions of this invention are valuable in the treatment of diseases in subjects, including human or animals, in which leukotrienes are a factor.

SUMMARY OF THE INVENTION

In a first aspect, this invention covers a compound of formula I

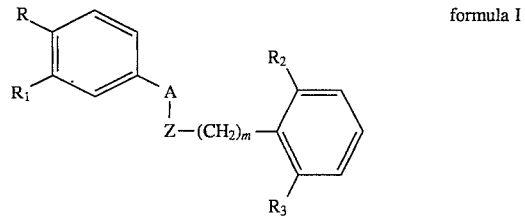

formula I or a pharmaceutically acceptable salt, where

A is $CH_2$ and Z is $S(O)q$ where q is 0, 1 or 2, $CH_2$, CHOH, C=O, or $NR_x$, or O; or A is C=O and Z is $NR_x$;

m is 0–5;

$R_x$ is hydrogen or lower alkyl;

R is $C_1$ to $C_{20}$-aliphatic, unsubstituted or substituted five-membered heteroaryl-$C_1$ to $C_{10}$-aliphatic—O—, unsubstituted or substituted phenyl-$C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic—O—, or R is unsubstituted or substituted phenyl-$C_1$ to $C_{10}$-aliphatic—O— where substituted phenyl has one or more radicals selected from the group consisting of lower alkoxy, lower alkyl, trihalomethyl, and halo;

$R_1$ is $R_4$, —($C_1$ to $C_5$ aliphatic)$R_4$, —($C_1$ to $C_5$ aliphatic)CHO, —($C_1$ to $C_5$ aliphatic)$CH_2OR_5$;

$R_2$ and $R_3$ are independently halo, lower alkoxy, $CF_3$, CN, or lower alkyl;

$R_4$ is tetrazol-5-yl or COOH or an ester or amide thereof; and $R_5$ is H, lower alkyl, $CH_3(CH_2)_{0-6}CO$ or phenyl$(CH_2)_{0-3}CO$.

In a further aspect, this invention relates to compositions comprising a compound of formula I, or a salt thereof, in admixture with a carrier. Included in these compositions are those suitable for pharmaceutical use and comprising a pharmaceutically acceptable excipient or carrier and a compound of formula I which may be in the form of a pharmaceutically acceptable salt.

These compounds can also be used for treating diseases, particularly psoriasis and inflammatory bowel disease.

Processes for making these compounds are also included in the scope of this invention, which processes comprise:
a) forming a salt, or
b) forming an ester,
c) oxidizing a thio ether to the sulfoxide or sulfone; or
d) forming a compound of formula I by treating a 6-halomethylpyridyl compound with the appropriate mercaptan, hydroxy, or amino compound.

GENERAL EMBODIMENTS

The following definitions are used in describing this invention.

"Aliphatic" is intended to include saturated and unsaturated radicals. This includes normal and branched chains, saturated or mono or poly unsaturated chains where both double and triple bonds may be present in any combination. The phrase "lower alkyl" means an alkyl group of 1 to 6 carbon atoms in any isomeric form, but particularly the normal or linear form. "Lower alkoxy" means the group lower alkyl—O—. "Acyl-lower alkyl" refers to the group (O)C-lower alkyl where the carbonyl carbon is counted as one of the carbons of the 1 to 6 carbons noted under the definition of lower alkyl. "Halo" refers to and means fluoro, chloro, bromo or iodo. The phenyl ring may be substituted with one or more of these radicals. Multiple substituents may be the same or different, such as where there are three chloro groups, or a combination of chloro and alkyl groups and further where this latter combination may have different alkyl radicals in the chloro/alkyl pattern.

The phrase "unsubstituted or substituted five-membered heteroaryl" means a five-membered aromatic ring which has one or more hetero atoms which are oxygen, sulfur or nitrogen. Examples of such rings are furyl, thienyl, tetrazolyl, thiazolyl, isothiazolyl, triazolyl, oxazolyl, isoxazolyl, thiadiazolyl, pyrrolyl, imidazolyl or pyrazolyl. Rings may be substituted with one or more lower alkyl groups, preferably methyl.

The phrase "a pharmaceutically acceptable ester-forming group" covers all esters which can be made from the acid function(s) which may be present in these compounds. The resultant esters will be ones which are acceptable in their application to a pharmaceutical use. By that it is meant that the esters will retain the biological activity of the parent compound and will not have an untoward or deleterious effect in their application and use in treating diseases.

Amides may be formed from acid groups. The most preferred amides are those where the nitrogen is substituted by hydrogen or alkyl of 1 to 6 carbons. The diethylamide is particularly preferred.

Pharmaceutically acceptable salts of the instant compounds are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner The parent compound, dissolved in a suitable solvent, is treated with an excess of an organic or inorganic acid, in the case of acid addition salts of a base, or an excess of organic or inorganic base where $R_4$ is COOH for example.

Oxides of the pyridyl ring nitrogen may be prepared by means known in the art and as illustrated herein. These are to be considered part of the invention.

If by some combination of substituents, a chiral center is created or another form of an isomeric center is created in a compound of this invention, all forms of such isomer(s) are intended to be covered herein. Compounds with a chiral center may be administered as a racemic mixture or the racemates may be separated and the individual enantiomer used alone.

As leukotriene antagonists, these compounds can be used in treating a variety of diseases associated with or attributing their origin or affect to leukotrienes, particularly $LTB_4$. Inflammatory diseases such as psoriasis and inflammatory bowel disease may be treated by applying or administering the compounds described herein. It is also expected that these compounds can be used to treat allergic diseases including those of a pulmonary and non-pulmonary nature. For example these compounds will be useful in antigen-induced anaphylaxis. They are useful in treating asthma, allergic rhinitis and irritable bowel disease. Ocular diseases such as uveitis, and allergic conjunctivitis can also be treated by these compounds.

These compounds show oral activity, that is they are absorbed in the gut and are active in vivo in test models. This is a unique feature as compared with other compounds of similar structure which are leukotriene antagonists..While other such compounds may be absorbed in the gut they do not demonstrate a therapeutic response in the target organ or disease state, in particular as relates to treating topical diseases such as psoriasis and the like.

Preferred compounds are those where R is $C_8$ to $C_{20}$ alkoxy, thienyl-$C_1$ to $C_{10}$ alkoxy, unsubstituted or substituted thiazolyl-$C_1$ to $C_{10}$ alkoxy, phenyl-$C_1$ to $C_{10}$ alkoxy or substituted-phenyl $C_1$ to $C_{10}$ alkoxy; $R_1$ is —$(C_1$–$C_3$alkyl)$R_4$, or —$(C_2$–$C_3$alkenyl)$R_4$ and $R_2$ and $R_3$, are both halo. The more preferred compounds are those where R is unsubstituted or substituted phenyl-$C_1$ to $C_{10}$ alkoxy, particularly the unsubstituted-phenyl$(CH_2)_{2-8}$—O— group, or the p-fluoro- or p-methoxyphenyl$(CH_2)_{2-8}$—O— group, or $CH_3(CH_2)_{7-9}$—O—; m is 0–5, most preferably 0, 1, or 2; $R_1$ is $HO_2C$—CH=CH—, or $HO_2C$—$CH_2CH_2$— or a salt, ester or amide derivative thereof. As regards A, the $CH_2$ group is preferred. As regards Z, $S(O)_q$ and O are preferred, and in $S(O)_q$ q is 1, 2 or 3. Another sub-group of preferred compounds are those where $R_2$ and $R_3$ are halo; methyl or methoxy, particularly where both are halo, methyl or methoxy. The 2,6-dichloro is a preferred compound. Specific preferred compounds are:

(E)-3-[5-[[(2,6-dichlorophenyl)thio]methyl]-2-(2-phenylethoxy)phenyl]-2-propenoic acid, (E)-3-[5-[[(2,6-dichlorophenyl)sulfinyl]methyl]-2-(2-phenylethoxy)phenyl]-2-propenoic acid, (E)-3-[5-[[(2,6-dichlorophenyl)sulfonyl]methyl]-2-(2-phenylethoxy)phenyl]-2propenoic acid, 3-[5-[[(2,6-dichlorophenyl)thio]methyl]-2-(2-phenylethoxy)phenyl]-2-propanoic acid, (E)-3-[[[[3-(2-carboxyethenyl)-4-[[8-(4-methoxyphenyl)octyl]oxy]phenyl]methyl]thio]methyl]benzoic acid, (E)-3-[[[[3-(2-carboxyethenyl)-4-[[8-(4-methoxyphenyl)octyl]oxy]phenyl]methyl]sulfinyl]methyl]benzoic acid, (E)-3-[[[[3-(2-carboxyethenyl)-4-[[8-(4-methoxyphenyl)octyl]oxy]phenyl]methyl]sulfonyl]methyl]benzoic acid, 3-[[[ 3-(2-carboxyethanyl)-4-[[ 8-(4-methoxyphenyl)octyl]oxy]phenyl]methyl]thio]methyl]benzoic acid, (E)-3-[5-[(phenylthio)methyl]-2-(2-phenylethoxy)phenyl]-2-propenoic acid, or (E)- 3-[5-[[(2,6-dichlorophenyl)thio]methyl]-2-(2-(4-fluorophenyl)ethoxy)phenyl]-2-propenoic acid, or a free acid thereof or another pharmaceutically acceptable salt.

Synthesis

Several methods, variations on the same process, have been used for preparing these compounds. In general, the approach taken was to first make the intermediates needed to make the R group, then to prepare a 5-halomethylbenzaldehyde compound, coupling it with a thiophenol or a phenylalkyl mercaptan, then manipulating the 2 position aldehyde or the 3 position hydroxyl group, the sequence is not critical to making the final product. Position 2 alkyl substituents are derived from the corresponding acrylate by catalytic hydrogenation, or some other form of reduction. Once the groups at positions 2 and 3 are prepared, salts, free acids, amides, alternative esters and the like can be prepared by conventional means.

Using the precursors prepared as per the noted PCT applications or which have been purchased from a commercial source, and the steps outlined in Scheme I, can be used to prepare compounds of formula I.

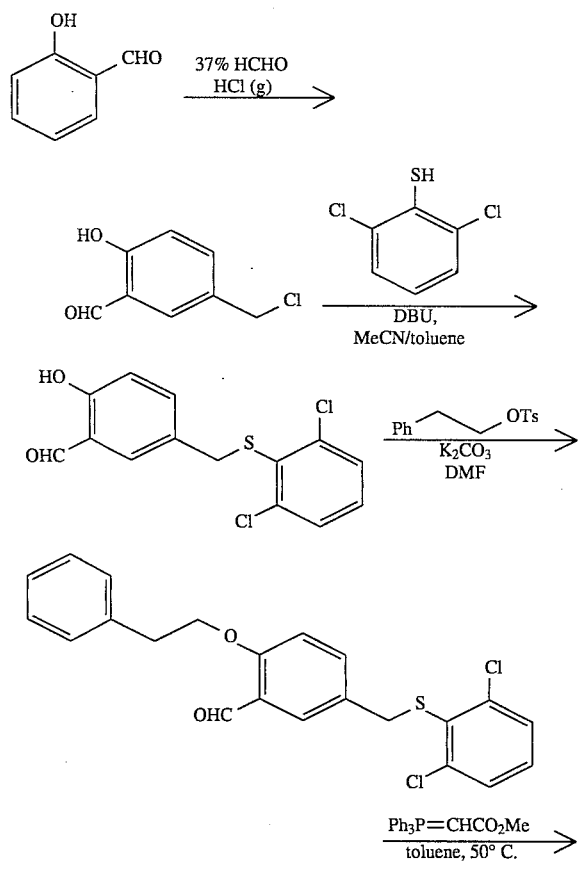

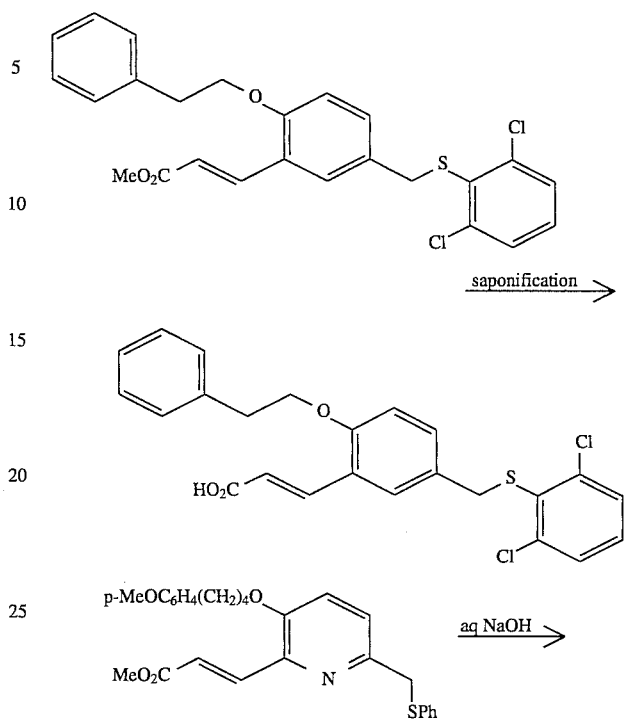

The salicylaldehyde is convened to the 5-chloromethylbenzaldehyde by combining the aldehyde with aqueous formaldehyde (37%) and concentrated hydrochloric acid, at a reduced temperature in the range of −10° to +10° C. or thereabouts. Gaseous HCl is then bubbled through the solution to saturate with HCl after which the solution is stirred for a period sufficient to effect the reaction at a reduced temperature, one which is about that of the temperature at which the reactants were combined initially. The product, the 5-(chloromethyl)-2-hydroxybenzaldehyde, should be formed as a white precipitate which can be recovered by conventional means.

The 5-(chloromethyl)-2-hydroxybenzaldehyde can then be coupled with any one of a number of thiophenols or phenhylalkyl mercaptans in the next step. A number of thiophenols and thioalkylphenyl compounds useful for making the right hand portion of formula I can be purchased from commercial sources. A list, not intended to be exhaustive, is as follows: 2,5-dichlorothiophenol, 2,6-dimethylthiophenol, 2,4-dichlorothiophenol, 2-chloro-6-methylthiophenol, 2-chloro-4-fluorothiophenol, 2,4-dichlorobenzyl thiol, 2-chloro-6-fluorobenzyl mercaptan, and 2,4-difluorobenzyl thiol. Other thiols can be made by published chemistry; that chemistry involves convening a haloalkylphenyl (the bromo form is preferred) compound to the corresponding mercaptan by treating the bromo compound with thiourea followed by base hydrolysis. Alternatively the thiophenols can be prepared by thermal rearrangement of the corresponding thiocarbamate followed by hydrolysis.

Coupling the thiol with 5-(chloromethyl)-2-hydroxybenzaldehyde is accomplished herein by using 1,8-diazabicyclo[5.4.0]undec-7-ene (DBU) and an aprotic solvent, for example acetonitrile or acetonitrile and toluene. A slight molar excess of the thiol is used relative to the aldehyde. Moisture is excluded from the system and an inert gas is used, for example argon. The reaction can be carried out at room temperature or there about. The reaction is run until all of the benzaldehyde is consumed; it can be monitored by thin layer chromatography.

Once the thiol is coupled with the chloride, the aldehyde and the hydroxyl group at positions 2 and 3 can be manipulated to provide the desired product as per formula I. The chemistry for manipulating these two positions can be found in published PCT applications PCT/US91/03398, PCT/US91/03772, PCT/US91/03940, and PCT/US91/03399.

The intermediates needed for forming those R groups, where the intermediates were not available commercially are prepared by the synthetic methods disclosed in noted PCT applications. All are incorporated herein by reference. Forming the ethers of position 3 is accomplished by the chemistry recited in these PCT applications. Likewise, manipulating the 2 position aldehyde is done by the chemistries set out in these self-same applications.

Base, or acid, can be used to hydrolyze any ester group, if so desired. The free acid can be obtained from the salt by acidifying a solution of the salt. Esters and amides can be prepared using standard reaction conditions and reagents. Tetrazoles are prepared from the corresponding acid halide, e.g., the acid chloride, by literage methods.

Pharmaceutical compositions of the present invention comprise a pharmaceutical carrier or diluent and some amount of a compound of the formula (I). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

Included within the scope of this disclosure is the method of treating a disease mediated by $LTB_4$ which comprises administering to a subject a therapeutically effective amount of a compound of formula I, preferably in the form of a pharmaceutical composition. For example, inhibiting the symptoms of an allergic response resulting from a mediator release by administration of an effective amount of a compound of formula I is included within the scope of this disclosure. The administration may be carried out in dosage units at suitable intervals or in single doses as needed. Usually this method will be practiced when relief of symptoms is specifically required. However, the method is also usefully carded out as continuous or prophylactic treatment. It is within the skill of the an to determine by routine experimentation the effective dosage to be administered from the dose range set forth above, taking into consideration such factors as the degree of severity of the condition or disease being treated, and so forth.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

No unacceptable toxicological effects are expected when these compounds are administered in accordance with the present invention.

Bioassays

The specificity of the antagonist activity of a number of the compounds of this invention is demonstrated by relatively low levels of antagonism toward agonists such as potassium chloride, carbachol, histamine and $PGF_2$.

The receptor binding affinity of the compounds used in the method of this invention is measured by the ability of the compounds to bind to [$^3$H]-$LTB_4$ binding sites on human U937 cell membranes. The $LTB_4$ antagonist activity of the compounds used in the method of this invention is measured by their ability to antagonize in a dose dependent manner the $LTB_4$ elicited calcium transient measured with fura-2, the fluorescent calcium probe. The methods employed have been disclosed in prior published PCT application PCT/US91/03772 which was fried 31 May 1991. The assays disclosed there are incorporated herein by reference.

SPECIFIC EMBODIMENTS

The following examples are given to illustrate how to make and use the compounds of this invention. These Examples are just that, examples, and are not intended to circumscribe or otherwise limit the scope of this invention. Reference is made to the claims for defining what is reserved to the inventors.

Example 1

Preparation of (E)-3-[5-[[(2,6-dichlorophenyl)thiolmethyl]-2-(2-phenylethoxy)phenyl]-2-propenoic acid 1 (a) 5-(Chloromethyl)-2-hydroxybenzaldehyde Salicylaldehyde (8.7 mL, 65.6 mmol) was added to a solution of aqueous formaldehyde (14 mL, 37%) and conc. HCl (42 mL) at 0° C. The reaction solution was then saturated with HCl gas and stirred at 10° C. An off-white precipitate was formed which was collected and washed with cold water. The solid was dissolved in $CH_2Cl_2$ and dried over $MgSO_4$. Evaporation of solvent provided 8.73 g of product. Mp 76°–79° C.

1(b) 5-[[(2. 6-Dichlorophenyl)thio]methyl]-2-hydroxybenzaldehyde

Chloride from Example 1(a) (4.32 g, 25.4 mmol), 2, 6-dichlorothiophenol (5.0 g, 27.9 mmol), and DBU (4.48 mL, 30 mmol) were stirred together at room temperature in a 1:2 solution of acetonitrile:toluene (72 mL) until complete consumption of chloride was indicated (TLC monitoring). The reaction solution was partitioned between EtOAc and water. The organic layer was separated and. washed with water and dried ($MgSO_4$). Evaporation of solvent provided a dark yellow solid which was triturated with cold EtOAc-hexane (1:8). Drying gave 5.04 g of product. Mp 114°–117° C.

1(c) 1-(4-Toluenesulfonate)-2-phenylethane

Phenethyl alcohol (3.0 g, 24.6 mmol) was dissolved in triethyl amine (7 mL) and $CH_2Cl_2$ (30 mL). The solution was cooled to 0° C. and tosyl chloride (5.15 g, 27.1 mmol) was added. The reaction was stirred at room temperature for 16 h. Reaction solution was diluted with EtOAc and the organic layer washed with 5% HCl, aq. $NaHCO_3$, and brine and dried ($MgSO_4$). Evaporation gave 6.84 g of product. NMR (250 MHz, $CDCl_3$) $\delta 7.69$ (d, 2H, aryl), 7.37 (m, 5H, aryl), 7.11 (d, 2H, aryl), 4.21 (t,J=6.86 Hz, 2H, $OCH_2$), 2.96 (t, J=6.80 Hz, 2H, benzylic), 2.42 (s, 3H, Me).

1(d) 5-[[(2,6-dichlorophenyl)thiolmethyl]-2-(2-phenylethoxy)phenyl]benzaldehyde

Phenol from Example 1(b) (500 mg, 1.6 mmol), rosylate from Example 1(c) (401 mg, 1.45 mmol), and powdered $K_2CO_3$ (276 mg, 2 mmol) were stirred together at room temperature in DMF (10 mL) for 48 h. The reaction solution was partitioned between EtOAc and water. The organic layer was separated and washed with water and dried ($MgSO_4$). The product was purified by flash column chromatography (silica, 4:1 hexane-EtOAc) to give 388 mg of product. Mp 54°–58 ° C. 1(e) Methyl (E)-3-[5-[[(2,6-dichlorophenyl] thiolmethyl]-2-(2-phenylethoxy)phenyl]-2 -propenoate Aldehyde from Example 1(d) (388 mg, 0.93 mmol) and methyl (triphenylphosphoranylidene)acetate (341 mg, 1.02 mmol) were heated together at 50° C. in toluene (7 mL) for 1.5 h. The cooled reaction solution was applied directly to a flash chromatography column (silica) and eluted with hexane followed by hexane-EtOAc (4:1) to yield 310 mg of product. Mp 80 –84 ° C.

1(f) Sodium (E)-3-[5-[[(2,6-dichlorophenyl]thio]methyl] -2-(2-phenylethoxy)phenyl]- 2-propenoante Ester from Example 1(e) (200 mg, 0.42 mmol) was dissolved in MeOH (0.85 mL) and THF (2.55 mL) and treated with 1N NaOH (0.84 mL, 0.84 mmol). The reaction was stirred at room temperature for 18 h. The solvents were evaporated and the product purified by reversed phase MPLC (RP- 18 silica, 0–80% MeOH-water). The product was isolated by lyophilization (133 mg). MS (ES) m/e 459 $[M+H]^+$.

Proceeding in a similar fashion, but substituting the appropriate intermedites and substrates for the ones detailed in (a) through (f) the following compounds are made as the sodium salt:

(E)-3-[5- [[(2,6-dichlorophenyl)sulfinyl]methyl]-2-(2-phenyl]-2-propenoic acid, (E)-3-[5-[[(2,6-dichlorophenyl)sulfonyl]methyl]-2-(2-phenylethoxy)phenyl]-2-propenoic acid, 3-[5-[[(2,6-dichlorophenyl)thio]methyl]-2-(2-phenylethoxy)phenyl]-2-propanoic acid, (E)-3-[[[[3-(2-carboxyethenyl)4-[[8-(4-methoxyphenyl)octyl]oxy]phenyl]methyl]thio]methyl]benzoic acid, (E)-3-[[[[3-(2-carboxyethenyl)-4-[[8-(4-methoxyphenyl)octyl]oxy]phenyl]methyl]sulfinyl]methyl]benzoic acid, (E)-3-[[[[3-(2-carboxyethenyl)-4-[[8-(4-methoxyphenyl)octyl]oxy]-phenyl methyl]sulfonyl]methyl]benzoic acid, 3[[[3-(2-carboxyethahyl)-4-[[8-(4-methoxyphenyl)octyl] -oxy]phenyl]methyl]thio]methyl]benzoic acid, (E)-3-[5-[(phenylthio)methyl]-2-(2-phenylethoxy)phenyl]-2-propenoic acid, or (E)-3-[5-[[(2,6-dichlorophenyl)thio]methyl]-2-(2-(4-fluorophenyl)ethoxy)phenyl]-2-propenoic acid.

Example 2

Formulations for pharmaceutical use incorporating compounds of the present invention can be prepared in various forms and with numerous excipients. Means for making various formulations can be found in standard texts such as Remington's Pharmaceutical Sciences, and similar publications and compendia. Specific examples of formulations are given below.

| OINTMENTS Hydrophyllic Petrolatum | |
|---|---|
| Ingredients | Amount (% Weight/weight) |
| Cholesterol | 30.0 g |
| Stearyl Alcohol | 30.0 g |
| White Wax | 78.0 g |
| Active Ingredient | 2.0 g |
| White Petrolatum | 860.0 g |

The stearyl alcohol, white wax and white petrolatum are melted together (steam bath for example) and cholesterol and the active ingredient are added. Stirring is commenced and continued until the solids disappear. The source of heat is removed and the mix allowed to congeal and packaged in metal or plastic tubes.

| Emulsion Ointment | |
|---|---|
| Ingredients | Amount (% W/W) |
| Methylparaben | 0.25 g |
| Propylparaben | 0.15 |
| Sodium Lauryl Sulfate | 10.0 g |
| Active Ingredient | 5.0 g |
| Propylene Glycol | 120.0 g |
| Stearyl Alcohol | 250.0 g |
| White Petrolatum | 250.0 g |
| Purified Water | QS to 1000.0 g |

The stearyl alcohol and white petrolatum are combined over heat. Other ingredients are dissolved in water, then this solution is added to the warm (ca 50° to 100° C.) alcohol/ petrolatum mixture and stirred until the mixture congeals. It can then be packed in tubes or another appropriate package form.

Example 3

Inhalation Formulation

A compound of formula I, 1 to 10 mg/ml, is dissolved in isotonic saline and aerosolized from a nebulizer operating at an air flow adjusted to deliver the desired amount of drug per use.

What is claimed is:

1. A compound of formula I

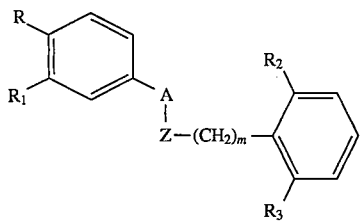

formula I or a pharmaceutically acceptable salt, where

A is $CH_2$ and Z is $S(O)_q$ where q is 0, 1 or 2, $CH_2$, CHOH, CO, $NR_x$, or O, or A is C=O and Z is $NR_x$;

m is 0–5;

$R_x$ is hydrogen or lower alkyl;

R is $C_1$ to $C_{20}$-aliphatic, unsubstituted or substituted five-membered heteroaryl-$C_1$ to $C_{10}$-aliphatic—O—, unsubstituted or substituted phenyl-$C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic—O—, or R is unsubstituted or substituted phenyl-$C_1$ to $C_{10}$-aliphatic—O— where substituted phenyl has one or more radicals selected from the group consisting of lower alkoxy, lower alkyl, trihalomethyl, and halo;

$R_1$ is $R_4$, —($C_1$ to $C_5$ aliphatic)$R_4$, —($C_1$ to $C_5$ aliphatic)CHO, —($C_1$ to $C_5$ aliphatic)$CH_2OR_5$;

$R_2$ and $R_3$ are independently, halo, lower alkoxy, $CF_3$, CN, or lower alkyl;

$R_4$ is tetrazol-5-yl or COOH; and $R_5$ is H, lower alkyl, $CH_3(CH_2)_{0-6}CO$ or phenyl$(CH_2)_{0-3}CO$; or a pharmaceutically acceptable salt thereof.

2. A compound of claim 1 where R is $C_8$ to $C_{20}$alkoxy, thienyl-$C_1$ to $C_{10}$ alkoxy, substituted thiazolyl-$C_1$ to $C_{10}$ alkoxy, phenyl-$C_1$ to $C_{10}$ alkoxy or substituted-phenyl $C_1$ to $C_{10}$ alkoxy; $R_1$ is —($C_1$–$C_3$alkyl)$R_4$, or —($C_2$–$C_3$alkenyl)$R_4$.

3. A compound of claim 2 where R is thien-2-ylethyloxy, thien-3-ylethyloxy, 3-methylthiazol-2-ylethyloxy, unsubstituted or substituted phenyl—$C_2$ to $C_{10}$ alkoxy or $CH_3(CH_2)7$-9—O—; m is 0, 1 or 2; $R_1$ is $HO_2C$—CH=CH—, or $HO_2C$—$CH_2CH_2$— or a salt, thereof.

4. A compound of claim 3 where $R_2$ and $R_3$ are both halo or both methyl.

5. A compound of claim 4 which is (E)-3-[5-[[(2,6-dichlorophenyl)thio]methyl]-2-(2-phenylethoxy)phenyl]-2-propenoic acid, (E)-3-[5-[[(2,6-dichlorophenyl)sulfinyl]methyl]-2-(2-phenylethoxy)phenyl]-2-propenoic acid, (E)3-[5-[[(2,6-dichlorophenyl)sulfonyl]methyl]-2-(2-phenylethoxy)phenyl]-2-propenoic acid, (E) 3-[5-[[(2,6-dichlorophenyl)thio]methyl]2-(2-phenylethoxy)phenyl]-2-propanoic acid, (E)-3-[[[[3-(2-carboxyethenyl)-4-[[8-(4-methoxyphenyl)octyl]oxy]phenyl]methyl]thio]methyl]benzoic acid, (E)-3-[[[[3-(2-carboxyethenyl)-4-[[8-(4-methoxyphenyl)octyl]oxy]phenyl]methyl]sulfinyl]methyl]benzoic acid, (E)-3-[[[[ 3-(2-carboxyethenyl)-4-[[8-(4-methoxyphenyl)octyl]oxy]phenyl]methyl]sulfonyl]methyl]benzoic acid, 3-[[[[3-(2-carboxyethanyl)-4-[[ 8-(4-methoxyphenyl)octyl]oxy]phenyl]methyl]thio]methyl]benzoic acid, (E)-3-[5-[(phenylthio)methyl]-2-(2-phenylethoxy)phenyl]-2-propenoic acid, or (E)-3-[5-[[(2,6-dichlorophenyl)thio]methyl]-2-(2-(4fluorophenyl)ethoxy)phenyl]-2-propenoic acid, or a free acid thereof or another pharmaceutically acceptable salt.

6. A method for treating psoriasis which comprises administering an effective amount of a compound of formula I according to claim 1 alone or admixed with a suitable carrier.

7. A composition comprising a pharmaceutically acceptable carrier and a compound according to claim 1.

8. A method for treating inflammatory bowel disease which comprises administering an effective amount of a compound of formula I according to claim 1 alone or admixed with a suitable carrier.

* * * * *